US00PP30061P3

(12) United States Plant Patent
Clos

(10) Patent No.: US PP30,061 P3
(45) Date of Patent: Jan. 8, 2019

(54) APPLE TREE NAMED 'ALPIGALA'

(50) Latin Name: *Malus domestica*
Varietal Denomination: Alpigala

(71) Applicant: International Fruit Obtention (IFO) GIE, Seiches sur le Loir (FR)

(72) Inventor: Thierry Clos, Manosque (FR)

(73) Assignee: International Fruit Obtentions (IFO) GIE, Seiches sur le Loir (FR)

( * ) Notice: Subject to any disclaimer, the term of this patent is extended or adjusted under 35 U.S.C. 154(b) by 0 days.

(21) Appl. No.: 15/330,390

(22) Filed: Sep. 12, 2016

(65) Prior Publication Data

US 2018/0077834 P1 Mar. 15, 2018

(51) Int. Cl.
*A01H 5/08* (2018.01)
*A01H 6/74* (2018.01)

(52) U.S. Cl.
USPC ..... Plt./162
CPC ..... *A01H 6/7418* (2018.05); *A01H 5/08* (2013.01)

(58) Field of Classification Search
USPC ..... Plt./162
CPC ..... A01H 5/0875
See application file for complete search history.

(56) References Cited

PUBLICATIONS

GTITM UPOVROM Citation for 'Alpigala' as per QZ PBR 20142091; Dec. 15, 2014; 1 page.*

* cited by examiner

*Primary Examiner* — Kent L Bell
(74) *Attorney, Agent, or Firm* — Michelle Bos Legal LLC

(57) ABSTRACT

'Alpigala' is a whole tree mutation of 'Gala', the fruit of which is notable for its early coloring, very dark overcolor, and strongly defined stripes.

5 Drawing Sheets

Latin name: *Malus domestica.*
Variety denomination: 'Alpigala'.

BACKGROUND OF THE VARIETY

'Alpigala' is a new and distinct variety of apple tree (*Malus domestica*). 'Alpigala' is a natural whole tree mutation of 'Gala' (U.S. Plant Pat. No. 3,637) discovered by the inventor in an established 'Gala' orchard at Manosque, France in 2010. Propagative material of the newly discovered tree was asexually reproduced by budding at Doué la Fontaine, France in 2010 and subsequently fruited through successive generations at Doué la Fontaine, France. 'Alpigala' has been observed to remain true to type over successive asexually propagated generations.

BRIEF DESCRIPTION OF THE VARIETY

'Alpigala' was first selected for its early coloring, very dark overcolor, and strongly defined stripes as compared to parent 'Gala' and other 'Gala' sports. Comparisons of 'Alpigala' to similar 'Gala'-type varieties 'Galaval' (U.S. Plant Pat. No. 19,909) and 'Biagent' (U.S. Plant Pat. No. 10,016) are shown in the following table:

TABLE 1

Comparison of 'Alpigala' to related and similar varieties

| | 'Alpigala' | 'Galaval' | 'Baigent' | 'Gala' |
|---|---|---|---|---|
| Overcolor | Dark purple brown | Dark red | Bright red | Light bright red |

TABLE 1-continued

Comparison of 'Alpigala' to related and similar varieties

| | 'Alpigala' | 'Galaval' | 'Baigent' | 'Gala' |
|---|---|---|---|---|
| Pattern of overcolor | Solid flush with strongly defined stripes | Solid flush with no defined stripes | Solid flush with strongly defined stripes | Heavily striped |
| Color development | Early, one month before harvest | Later, one week before harvest | Early | Late |

BRIEF DESCRIPTION OF THE PHOTOGRAPHS

Figure 1:
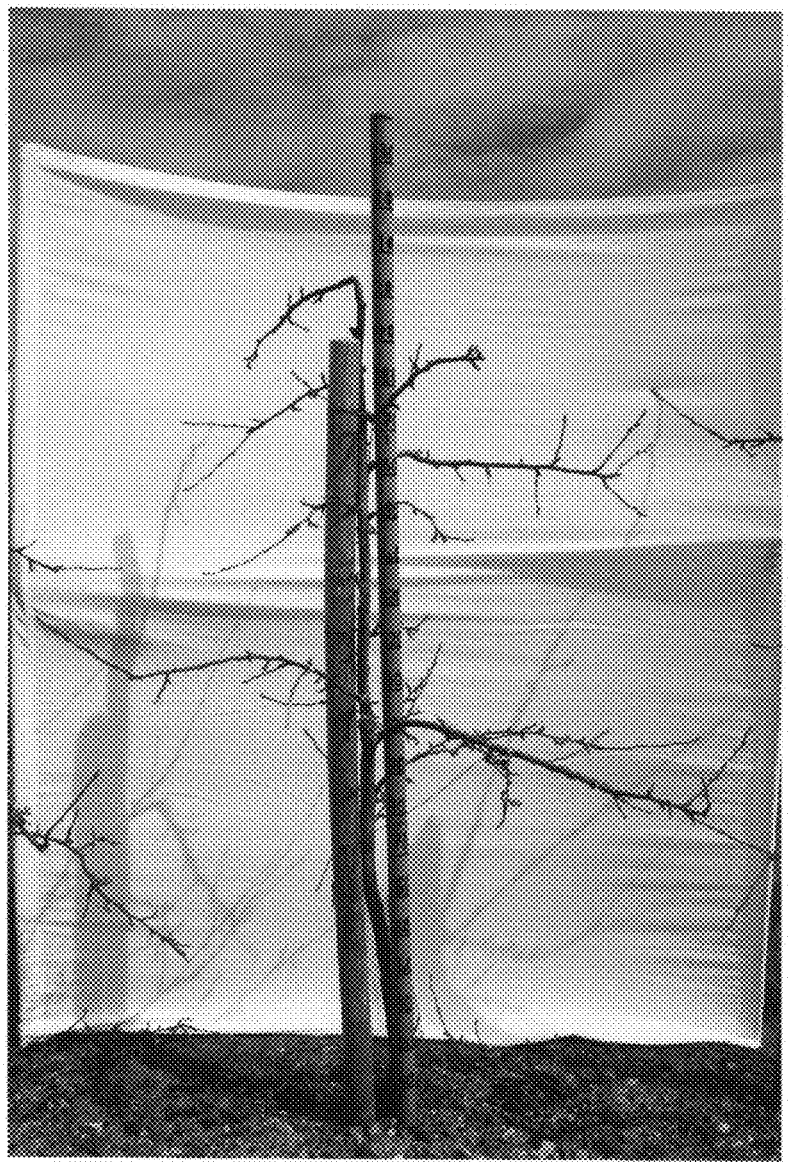
Figure 2:
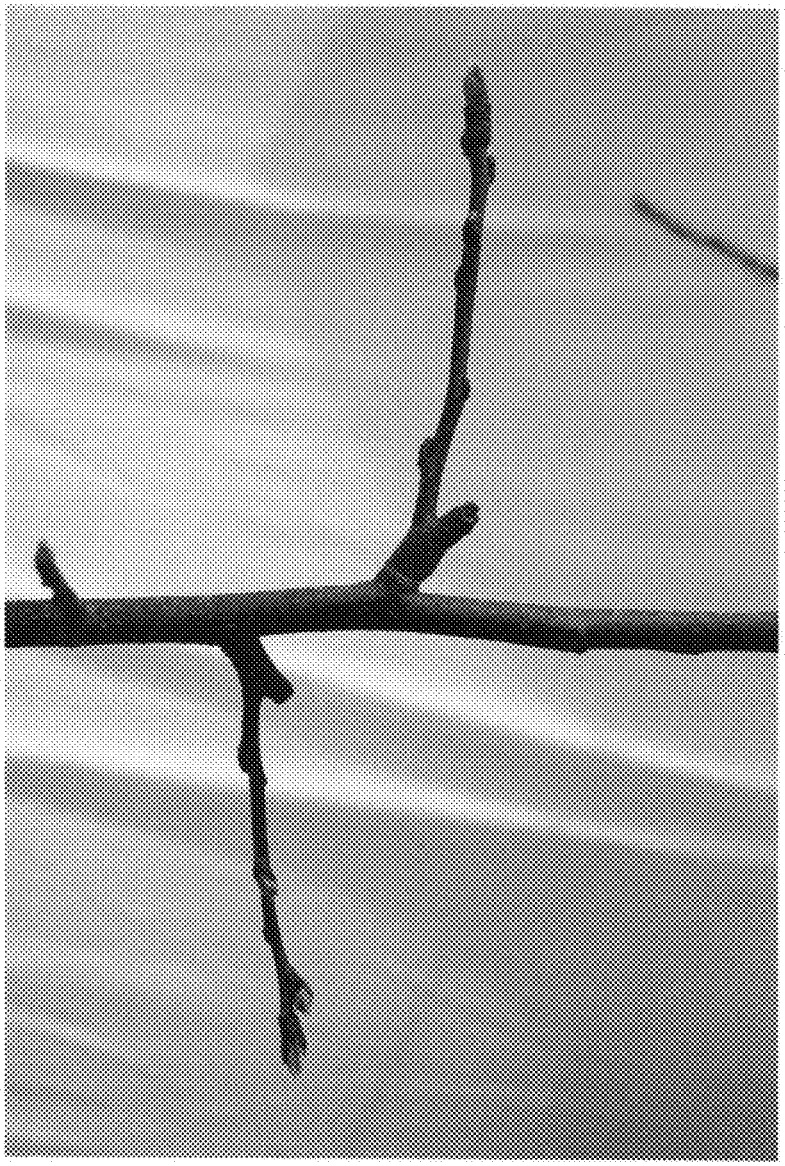
Figure 3:
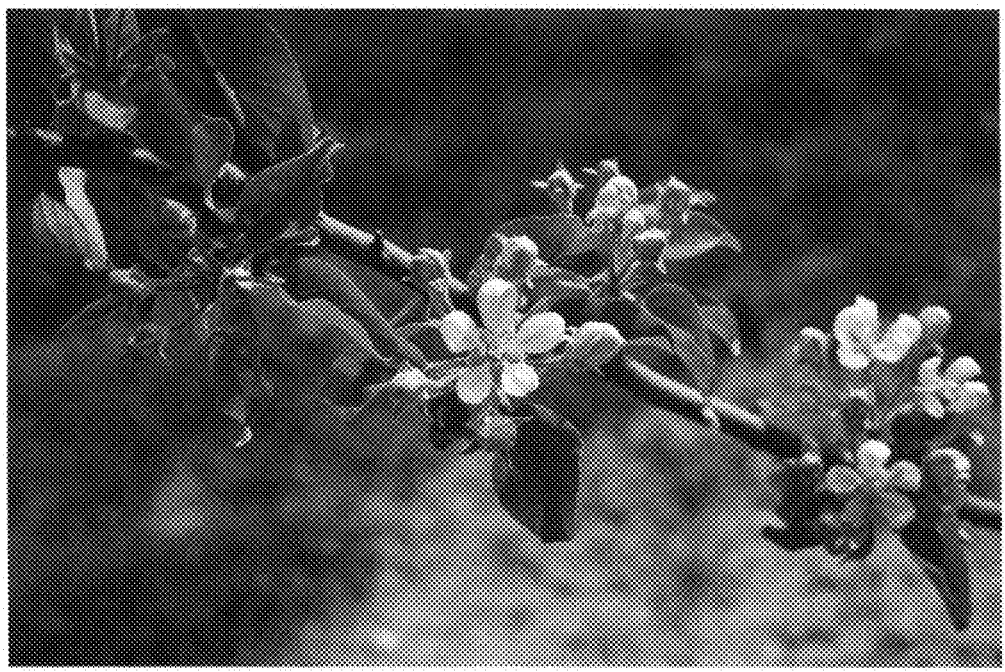
Figure 4:
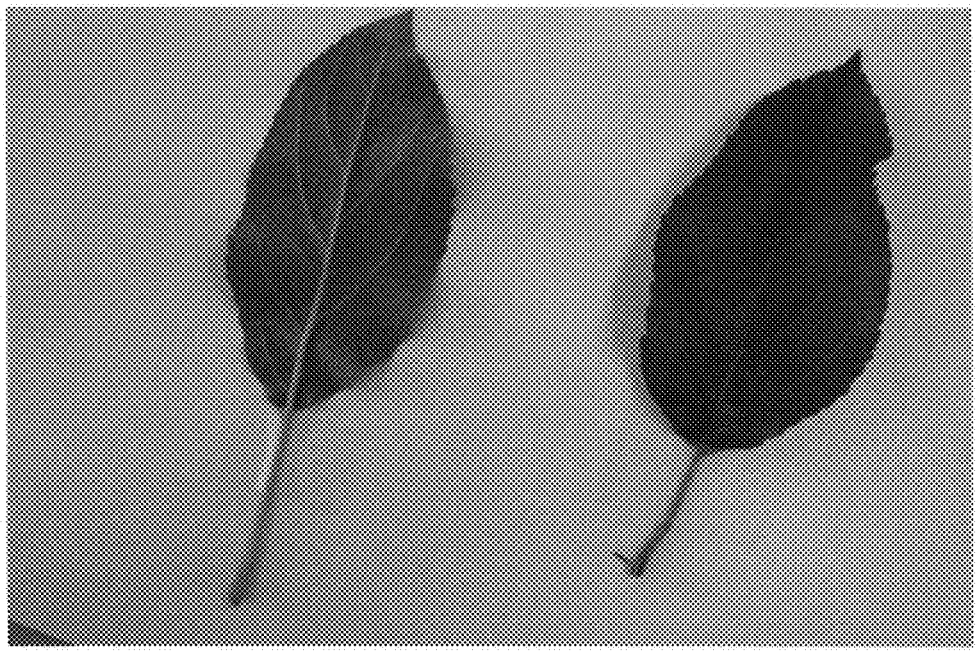
Figure 5:
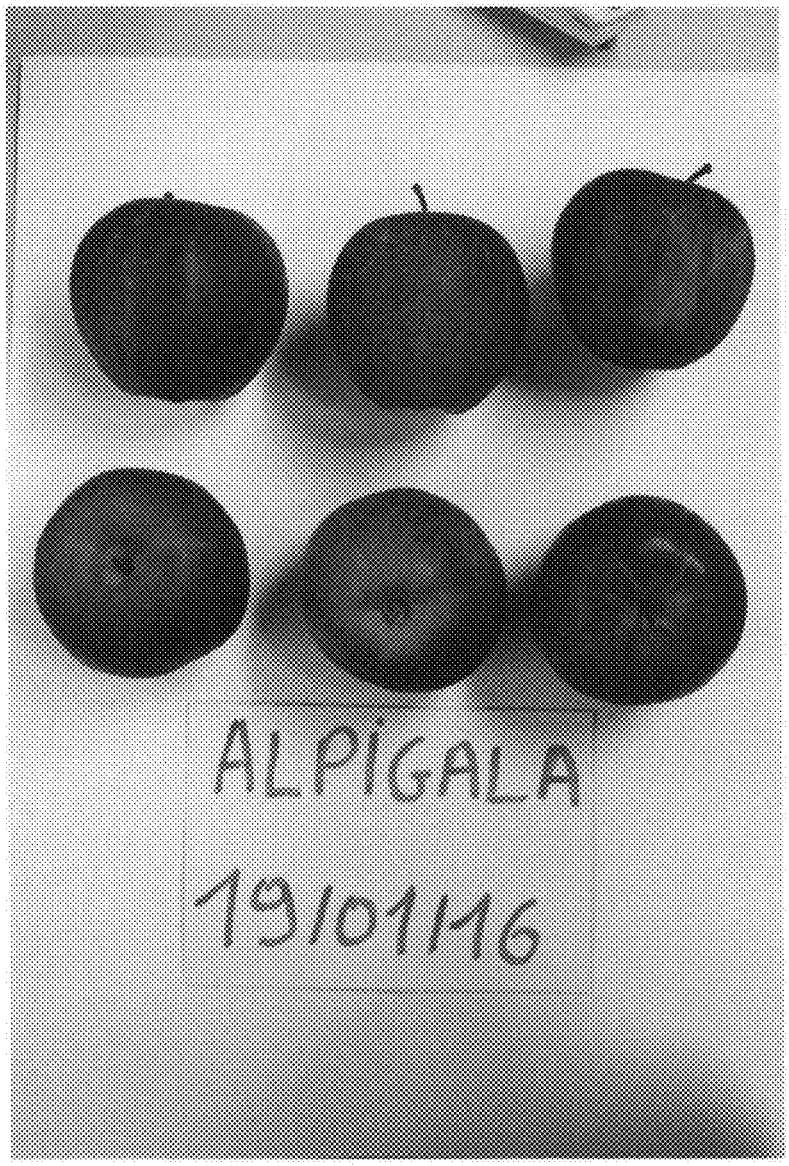

FIG. 1. shows an 'Alpigala' tree;
FIG. 2 shows shoots and buds on an 'Alpigala' tree;
FIG. 3 shows blossoms and leaves on an 'Alpigala' tree;
FIG. 4 shows leaves of 'Alpigala'; and
FIG. 5 shows fruit of 'Alpigala'.

DETAILED BOTANICAL DESCRIPTION OF THE VARIETY

The following-detailed botanical description is based on observations made during 2015 and 2016 at Seiches sur le Loir, France of 3 and 4 year old trees grown on Pajam® 2 Cepiland rootstock (not patented). All colors are described according to The Royal Horticultural Society Mini Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor*.—Medium.
- *Type*.—Ramified.
- *Habit*.—Spreading.
- *Height*.—2.20 m.
- *Trunk diameter* (*at* 30 *cm above the graft*).—Medium (average 40 mm).
- *Bark texture*.—Smooth.
- *Bark coloration*.—Grey N200C.

Branch (fruiting branches located at around 1 m above the graft union):
- *Length*.—Long, average 1.20 m.
- *Diameter*.—Large, average 20 cm.
- *Crotch angle*.—70 to 90°.
- *Bark color*.—Grey N200C.
- *Lenticel length*.—1 mm.
- *Lenticel shape*.—Round.
- *Lenticel color*.—Light yellow 8C.
- *Number of lenticels per cm*$^2$.—7 per cm$^2$.

One year old shoot:
- *Length*.—Short to medium, average 20 cm.
- *Color*.—Brown N199C.
- *Pubescence*.—Medium.
- *Thickness*.—Thin, average 3.5 mm.
- *Internode length*.—Medium, average 18 mm.
- *Pubescence*.—Medium.
- *Lenticel diameter*.—1 mm.
- *Lenticel height*.—0.5 mm.
- *Lenticel shape*.—Round.
- *Lenticel color*.—Light yellow 4D.
- *Number of lenticels per cm*$^2$.—7 per cm$^2$.

Flower buds:
- *Quantity per spur*.—1 to 3.
- *Shape*.—Round to conical.
- *Length*.—Small to medium, average 11 mm.
- *Diameter*.—Small to medium, average 12 mm.
- *Color*.—Red purple N57A.

Flowers:
- *Diameter of fully open flower*.—Small to medium, average 29 mm.
- *Flower depth*.—18.6 mm.
- *Relative position of petal margin*.—Overlapping.
- *Fragrance*.—Medium.
- *Number per cluster*.—5 to 6.
- *Date of first bloom*.—April 15 in Loire Valley, France.
- *Date of full bloom*.—April 20 in Loire Valley France.
- *Pollination requirement*.—'Braeburn', 'Granny Smith', or any other variety flowering at the same time.

Petals:
- *Number per flower*.—5.
- *Shape*.—Ovoid.
- *Length*.—Medium, average 17 mm.
- *Width*.—Medium, average 13 mm.
- *Apex*.—Round.
- *Base*.—Conical-pointed.
- *Margin*.—Smooth.
- *Color of upper surface*.—White N155C.
- *Color of lower surface*.—White N155B.

Pistils:
- *Quantity*.—5.
- *Length*.—Medium, average 13 mm.
- *Color*.—Yellow green N144C.

Stigma:
- *Diameter*.—Small to medium, average 0.6 mm.
- *Color*.—Yellow green 150B.

Style:
- *Size*.—Long, average 11 mm.
- *Color*.—Yellow green 145A.

Ovary:
- *Diameter*.—Medium, average 2 mm.
- *Color*.—Green 140A.

Anthers:
- *Quantity*.—Numerous, average 13 per flower.
- *Length*.—Medium, average 2 mm.
- *Presence of pollen*.—Present, abundant.
- *Color of pollen*.—Yellow 3C.

Pedicel:
- *Length*.—Medium to long, average 22 mm.
- *Diameter*.—Quite thin, 1.5 mm.
- *Color*.—Green 143B.

Sepals:
- *Quantity*.—5 per flower.
- *Length*.—9.3 mm.
- *Width*.—3.8 mm.
- *Apex*.—Pointed.
- *Color*.—Upper surface — Yellow-green 145A.
- *Color*.—Lower surface — Light green 138D.
- *Shape*.—Conical pointed.
- *Margin*.—Smooth, pubescent.

Leaves:
- *Shape*.—Elliptic.
- *Length*.—Medium, average 88 mm.
- *Width*.—Narrow, average 43 mm.
- *Length/width ratio*.—Medium to large (2.05).
- *Blade margin*.—Serrate.
- *Apex*.—Acuminate.
- *Base shape*.—Oblique.
- *Color of upper surface*.—Dark green 137A (late summer).
- *Color of lower surface*.—Green 137C (late summer).
- *Attitude in relation to shoot*.—Outwards to downwards.

Petiole:
- *Length*.—Long, average 35 mm.
- *Diameter*.—Thin, average 1.5 mm.
- *Coloration*.—Green 137C.

Fruit:
- *Quantity per cluster*.—2 to 4.
- *Diameter*.—73 mm.
- *Height*.—63 mm.
- *Weight*.—164 g.
- *Ratio of height to width*.—Medium, 0.86.
- *General shape in profile*.—Conical.
- *Position of maximum diameter*.—Middle.
- *Ribbing*.—Moderate.
- *Crowning at calyx end*.—Moderate.
- *Length of eye*.—5 mm.
- *Width of eye*.—5 mm.
- *Depth of eye*.—6 mm.
- *Aperture of eye*.—Closed.
- *Length of sepal*.—Long.
- *Bloom of skin*.—Weak.
- *Greasiness of skin*.—Weak.
- *Amount of over color*.—Very high.

*Over color of skin*.—Dark purple brown N77A.
*Background color*.—Light yellow 15D.
*Intensity of over color*.—Very intense.
*Pattern of over color*.—Solid flush with strongly defined stripes.
*Amount of russet around stalk cavity*.—Small.
*Amount of russet on cheeks*.—Very weak.
*Area of russet around eye basin*.—Absent.
*Length of stalk*.—Medium, 26 mm.
*Thickness of stalk*.—Medium, 2 mm.
*Depth of stalk cavity*.—Medium, 15 mm.
*Width of stalk cavity*.—Narrow, 27 mm.
*Depth of eye basin*.—Shallow, 12 mm.
*Width of eye basin*.—Medium, 24 mm.
*Firmness of flesh*.—Medium to firm, 7.1 kg/cm$^2$.
*Flesh texture*.—Medium to fine.
*Aroma*.—Moderately aromatic, slightly sweet.
*Juiciness*.—Medium to high.
*Brix*.—11° Brix.
*Flesh color*.—Light yellow 4D.
*Stem coloration*.—Dark purple red 187A.

Fruit locules:
*Quantity per fruit*.—5.
*Length*.—12 mm.
*Width*.—6 mm.

Seeds:
*Quantity per fruit*.—5 on average.
*Length*.—9 mm.
*Width*.—5 mm.
*Shape*.—Truncate ovoid.
*Coloration*.—Dark purple red 53A.

Harvest:
*Time for harvest*.—Early, last week of August (similar to Galaxy).
*Number of picks*.—One to two picks.
*Fruit load per tree*.—60 fruits (about 10 kg) on third leaf trees in 2016.

Disease resistance/susceptibility: None noted.
Winter hardiness: Hardy in region tested, USDA Hardiness Zone 9a.
Market use: Fresh.
Eating quality: Excellent — crisp, juicy and sweet.
Storageability: About 4 months in cold storage, up to about 7 months in controlled atmosphere storage.

I claim:

1. A new and distinct apple tree as described and illustrated herein.

* * * * *